United States Patent [19]

Ernst

[11] Patent Number: 5,585,398
[45] Date of Patent: Dec. 17, 1996

[54] TOPICAL ANESTHETIC COMPRISING LIDOCAINE, ADRENALINE, AND TETRACAINE, AND ITS METHOD OF USE

[76] Inventor: Amy A. Ernst, 26 Maryland Dr., New Orleans, La. 70124

[21] Appl. No.: 276,101

[22] Filed: Jul. 15, 1994

[51] Int. Cl.$^6$ ................................................. A61K 31/24
[52] U.S. Cl. .......................... 514/537; 514/536; 514/535; 514/626; 514/817
[58] Field of Search .................................. 514/626, 817, 514/535, 536, 537

[56] References Cited

U.S. PATENT DOCUMENTS

| | | | |
|---|---|---|---|
| 3,868,445 | 2/1975 | Ryde et al. | 424/14 |
| 3,898,339 | 8/1975 | Adams et al. | 424/251 |
| 3,957,996 | 5/1976 | Adams et al. | 424/253 |
| 4,006,218 | 2/1977 | Sipos | 424/54 |
| 4,029,794 | 6/1977 | Adams et al. | 424/253 |
| 4,057,582 | 11/1977 | Dunnigan et al. | 260/574 |
| 4,105,760 | 8/1978 | Szejtli et al. | 424/180 |
| 4,200,098 | 4/1980 | Ayer et al. | 128/260 |
| 4,285,987 | 8/1981 | Ayer et al. | 427/3 |
| 4,320,759 | 3/1982 | Theeuwes | 128/260 |
| 4,474,751 | 10/1984 | Haslam et al. | 424/78 |
| 4,562,060 | 12/1985 | Broberg et al. | 424/28 |
| 4,668,506 | 5/1987 | Bawa | 424/429 |
| 4,861,760 | 8/1989 | Mazuel et al. | 514/54 |
| 4,945,084 | 7/1990 | Packman | 514/53 |
| 4,966,773 | 10/1990 | Gressel et al. | 424/489 |
| 5,077,033 | 12/1991 | Viegas et al. | 514/668 |
| 5,147,294 | 9/1992 | Smith et al. | 604/49 |
| 5,149,320 | 9/1992 | Dhaliwal et al. | 604/49 |
| 5,196,405 | 3/1993 | Packman | 514/53 |
| 5,234,957 | 8/1993 | Mantelle | 514/772 |
| 5,252,318 | 10/1993 | Joshi et al. | 424/78.04 |
| 5,261,903 | 11/1993 | Dhaliwal et al. | 604/416 |

OTHER PUBLICATIONS

Schilling, C. G. et al., "Tetracaine, Epinephrine, Cocaine (TAC) vs Lidocaine, Epinephrine, Tetracaine (LET) for Anesthesia of Lacerations in Children", *American Journal of Diseases of Children*, (Apr. 1993), p. 427, No. 48.

Schilling, C. G. et al., "Tetracaine, Epinephrine, Cocaine (TAC) vs Lidocaine, Epinephrine, Tetracaine (LET) for Anesthesia of Lacerations in Children", *Annals of Emergency Medicine*, (Feb. 1995), p. 203.

Ernst, Amy A. et al., "Lidocaine Adrenaline Tetracaine Gel Versus Tetracaine Adrenaline Cocaine Gel for Topical Anesthesia in Linear Scalp and Facial Lacerations in children Aged 5 to 17 Years", *Pediatrics*, (Feb. 1995), pp. 255–258.

Ernst, Amy A. et al., "LAT (Lidocaine–Adrenaline–Tetracaine) Versus TAC (Tetracaine–Adrenaline–Cocaine) for Topical Anesthesia in Face and Scalp Lacerations", *American Journal of Emergency Medicine*, (Mar. 1995) pp. 151–154.

Adriani et al., "Fatalities following topical application of local anesthetics to mucous membranes", *JAMA* 1956; 162 (17):1527–1530.

Campbell et al., "Absorption of local anethetics", *JAMA* 1958; 168(7):873–877.

Adriani, "The clinical pharmacology of local anesthetics" *Clinical Pharmacology and Therapeutics*, vol. I., No. 5, 645–673 (1960).

Adriani et al., "Clinical effectiveness of drugs used for topical anesthesia", *JAMA* 1964; 188(8): 711–716.

DiFazio, "Local anesthetics: Action, metabolism and toxicity", *Otolaryngologic Clinics of North America*, 1981; 14(3): 515–519.

Mofenson et al., "Lidocaine toxicity from topical mucosal application", *Clinical Pediatrics*, Mar. 1983; 22(3): 190–192.

Beyer et al., "Systemic Toxicity from Tetracaine Pharyngeal Anesthesia", *Digestive Diseases and Sciences*, vol. 35, No. 2 (Feb. 1990), p. 280.

Wase et al., "XAP –an Alternative to Cocaine for Topical Anesthesia", *Annals of Emergency Medicine*, 22:11 (Nov. 1993), pp. 1776–1777.

*Primary Examiner*—Brian M. Burn
*Attorney, Agent, or Firm*—Pravel, Hewitt, Kimball & Krieger

[57] ABSTRACT

A topical anesthetic includes about 1–10% by weight lidocaine hydrochloride, about 0.01–0.10% by weight adrenaline, and about 0.25–4% by weight tetracaine hydrochloride, preferably in an aqueous base with about 2% benzyl alcohol or in a gel including about 3% hydroxyethyl cellulose. The topical anesthetic has been found to be at least as effective as TAC (tetracaine hydrochloride, adrenaline, cocaine), but with fewer harmful side effects and at a greatly reduced cost (about 1/10 of the cost of TAC).

26 Claims, No Drawings

TOPICAL ANESTHETIC COMPRISING LIDOCAINE, ADRENALINE, AND TETRACAINE, AND ITS METHOD OF USE

BACKGROUND OF THE INVENTION

1. Field of the Invention

The present invention relates to topical anesthetics. More particularly, the present invention relates to topical anesthetics for lacerations.

2. General Background of the Invention

There has been a long-felt need for a topical anesthetic that affords painless, safe application, does not contain narcotics or controlled substances, and has a maximum safety with complete anesthesia.

The topical anesthetic TAC (tetracaine, adrenaline, cocaine) was introduced by Pryor et al. in 1980. It was a revolutionary new approach to laceration repair (1) (the numbers in parentheses refer to the numbers of the articles cited in the Appendix—all of these articles are hereby incorporated by reference). However, there have been varying reports of its efficacy, safety, side effects, and wound infection rates.

Several studies since that of Pryor et al. have shown varying efficacy of the TAC solution, and have compared the efficacy of TAC to injected lidocaine in application and anesthetic properties (2–5).

TAC's effectiveness and acceptance as an adequate topical anesthetic for laceration repair has been demonstrated in pediatric patients in several studies. TAC was found to be effective in lacerations by Bonadio, (4) and provided adequate anesthesia and was better received by patients in comparison to injected lidocaine according to Hegenbarth (3) and Anderson (2). Bonadio demonstrated good results with use of a cocaine-adrenaline gel in pediatric patients (21).

Recent studies have demonstrated increased risks with the use of TAC solutions. Seizures and even death, presumably secondary to absorption of the cocaine component of TAC, have been reported (6,7,8). Animal studies and clinical human trials have demonstrated presence of cocaine and metabolites in urine (9,10) and blood (11,12) after use of TAC solution for laceration repair in a substantial number of patients. Another theoretical risk has been the higher incidence of local wound complications seen in animal studies (13,14), but this has not been borne out in clinical studies.

To address the toxic side effects of TAC, several recent studies have attempted to compare altered formulations of the components. These alterations include decreasing the amount of cocaine (15,16), using TAC with and without cocaine (17), cocaine alone, (18) tetracaine alone, (19) or eliminating the tetracaine component (20,21). None of these formulations were more effective than TAC, and most were not as effective (especially when cocaine was omitted).

Previous studies of topical anesthetics for laceration repair began to appear in 1980 when Pryor et al. introduced TAC. TAC, applied as a topical anesthetic, was found to be equal to injected lidocaine in all locations for anesthetic efficacy and better accepted by patients and families (1). Some subsequent studies have shown TAC (applied topically) to be as effective as injected lidocaine in all locations (2,5) while other studies have shown TAC to be effective only on the face and scalp (3,4,19).

Particular reference has been made to pediatric patients in several studies. A topically applied anesthetic that is painless to apply and effective is desirable in this patient population in particular (2,3,4).

Studies of the infections associated with TAC use began to appear in 1982. In his animal study Barker reported TAC-treated wounds had increased infection rates, necrosis, and higher bacterial counts compared to control wounds (13). In 1990, however, Martin et al. reported that in contaminated porcine wounds TAC did not cause an increase in bacterial proliferation compared to lidocaine infiltration (14). Generally, clinical studies comparing TAC versus lidocaine have not shown greater infection rates in TAC treated wounds (1–5,15,17–19).

Other problems associated with TAC use began to appear in the literature. Mucous membrane absorption may result in hyperexcitability, euphoria, tachcardia, hypertension, and seizures (6). Seizures have been reported with application to burns (29). Dripping into the eyes has been reported with resultant corneal abrasions (30,31). Two deaths have been reported secondary to TAC application close to mucous membranes. One case was a seven month old who had TAC applied twice with dripping into the mouth and nose (8). The other was a four year old with application directly to the tongue (32). These problems are likely to be due to absorption of components of TAC solution. Animal and clinical studies of urine and plasma levels of components of TAC have demonstrated positive cocaine and metabolite levels. Interestingly, tetracaine levels were not measurable in any of these studies (9,11,12).

Because of problems associated with TAC absorption, especially to mucous membranes, several studies have attempted to change the formulation of TAC to make it potentially less toxic without affecting the anesthetic ability. Prior attempts at altering TAC to improve its efficacy have compared TAC to solutions with either differing concentrations of all of the components of TAC or solutions of one or two of the components. Schaffer compared TAC with and without cocaine and concluded cocaine provided a significant proportion of the anesthetic property of TAC (17). In a previous study of TAC versus cocaine alone, the cocaine solution did not work as well as the TAC solution (18). Others have shown that tetracaine alone is not effective (19, 33). Smith et al. compared three different formulations of tetracaine, adrenaline and cocaine and found a 4% cocaine solution worked as well as a 7% or 11.8% solution (15). Bonadio and Wagner showed that when they halved the amount of cocaine in the TAC solution, it still worked effectively (16) and that cocaine adrenaline (CA) was as effective as TAC. They recommended removal of the tetracaine component (20). A gel form of CA was also introduced by Bonadio and found to be effective in a non-randomized non-blinded study and perhaps may require less solution for effective anesthesia (21). Removal of the controlled substance component (cocaine), which appears to be the major cause of TAC-associated toxicity, has never been possible without loss of efficacy of the solution (17, 19).

Topical lidocaine and tetracaine have both been used safely on mucous membranes in the past (33–36). Thrasher et al. recommend topical lidocaine use for bladder biopsy, (33) Rowbother and Fields recommend its use for herpetic neuralgia, (34) and Borfeldt et al. recommend it for burns (35). In studies by Adriani and Zepenick tetracaine was found to be one of the most effective and longest lasting topical anesthetics (more effective than cocaine or lidocaine) (37). Tetracaine has been used in topical application for many years in endoscopic procedures (38) and recently for insertion of intravenous catheters in intact skin (39). It has been a part of the TAC mixture since its introduction by Pryor et al. (1).

Toxicity related to lidocaine and tetracaine have in the past involved mucous membrane application with large concentrations applied or ingested. Seizures were caused in an infant ingesting 80 cc viscous lidocaine over an undetermined time period (40) and in an eleven month old being treated for teething pain (41) and in a two year old who drank viscous lidocaine in error (42). Adriani et al. reported a large series of tetracaine fatalities when used topically on mucous membranes for endoscopic procedures. However in most instances more than 160 mg were used (43).

SUMMARY OF THE INVENTION

The most optimum characteristics of a local anesthetic for laceration repair are to provide painless application, efficacy, and safety, without distorting tissue planes. In addition, it is desirable to minimize exposure of health care workers to needles.

The topical anesthetic of the present invention has these advantageous characteristics. The present invention comprises a pharmaceutical composition for use as a topical anesthetic, the composition comprising: an effective, though not excessive, amount of a lidocaine component; an effective, though not excessive, amount of an adrenaline component or other vasoconstrictor; and an effective, though not excessive, amount of a tetracaine component.

The topical anesthetic of the present invention preferably contains 1% to 10% lidocaine hydrochloride, 0.01% to 0.10% adrenaline component, and 0.25% to 4% tetracaine hydrochloride. A suitable, inert, pharmaceutically acceptable carrier is used for the composition comprising the lidocaine component, adrenaline component or other vasoconstrictor, and tetracaine component. The topical anesthetic of the present invention can be in liquid form, in which case the carrier could comprise water. The topical anesthetic of the present invention can be in gel form, in which case the carrier could comprise hydroxyethyl cellulose or other gels.

The amount of lidocaine is preferably at least 1% by weight lidocaine hydrochloride, the amount of adrenaline component is at least 0.01% by weight, and the amount of tetracaine is at least 0.25% by weight tetracaine hydrochloride. Benzyl alcohol can be included in the composition. It is useful as a preservative; it also has some anesthetic properties.

A preservative means can be used for preserving the composition.

The active ingredients of the composition of the present invention are lidocaine, an adrenaline component or another vasoconstrictor, and tetracaine.

The present invention comprises a method of inducing local anesthesia in a subject having a laceration, comprising applying topically to the laceration a therapeutically effective amount of a topical pharmaceutical composition (a topical anesthetic) comprising effective, but not excessive, amounts of lidocaine, tetracaine, and an adrenaline component or other vasoconstrictor.

The pharmaceutical composition can comprise 1% to 10% by weight lidocaine hydrochloride, 0.01% to 0.10% by weight adrenaline component, and 0.25% to 4% by weight tetracaine hydrochloride. It is believed that these ranges are the optimal percentages. It is believed that going below this range would reduce effectiveness. It is believed that going above this range would increase risk of side effects, without increasing effectiveness.

To avoid undesired adverse reactions, the topical anesthetic is not applied to mucous membranes.

It is believed that vasoconstrictors other than the adrenaline component (and other components which retard absorption of the tetracaine and lidocaine, thus making the anesthetic properties last longer) could be used in place of the adrenaline component with equal efficacy, provided that they are provided in the proper form and concentration.

DETAILED DESCRIPTION OF THE PREFERRED EMBODIMENT

Despite the presence of cocaine in the blood after TAC application, no studies have shown demonstrable levels of tetracaine. The inventor has observed that, if the cocaine component is absorbed and is responsible for the risks, it would be of value to formulate a solution with the same efficacy, but without the risks.

The present invention is a topical anesthetic which has been found to be at least as effective as TAC, but without the risks associated therewith.

The topical anesthetic of the present invention preferably contains 1% to 10% lidocaine hydrochloride, 0.01% to 0.10% adrenaline component, and 0.25% to 4% tetracaine hydrochloride. The topical anesthetic of the present invention is in a suitable carrier.

The topical anesthetic of the present invention preferably contains at least 1% lidocaine hydrochloride, more preferably at least 2% lidocaine hydrochloride, and most preferably at least 4% lidocaine hydrochloride. It preferably contains not more than 10% lidocaine hydrochloride, more preferably contains not more than 6% lidocaine hydrochloride, and most preferably contains not more than 4% lidocaine hydrochloride.

The preferred range of lidocaine hydrochloride in the topical anesthetic of the present invention is 1% to 10%. More preferably, the range of lidocaine hydrochloride in the topical anesthetic of the present invention is 2% to 6%. Most preferably, the amount of lidocaine hydrochloride in the topical anesthetic of the present invention is about 4%.

The topical anesthetic of the present invention preferably contains at least 0.01% adrenaline component, more preferably at least 0.025% adrenaline component, and most preferably at least 0.05% adrenaline component. It preferably contains not more than 0.10% adrenaline component, more preferably contains not more than 0.075% adrenaline component, and most preferably contains not more than 0.05% adrenaline component.

The preferred range of adrenaline component in the topical anesthetic of the present invention is 0.01% to 0.10%. More preferably, the range of adrenaline component in the topical anesthetic of the present invention is 0.025% to 0.075%. Most preferably, the amount of adrenaline component in the topical anesthetic of the present invention is about 0.05%.

The topical anesthetic of the present invention preferably contains at least 0.25% tetracaine hydrochloride, more preferably at least 0.5% tetracaine hydrochloride, and most preferably at least 1% tetracaine hydrochloride. It preferably contains not more than 4% tetracaine hydrochloride, more preferably contains not more than 2% tetracaine hydrochloride, and most preferably contains not more than 1% tetracaine hydrochloride.

The preferred range of tetracaine hydrochloride in the topical anesthetic of the present invention is 0.25% to 4%. More preferably, the range of tetracaine hydrochloride in the topical anesthetic of the present invention is 0.5% to 2%.

Most preferably, the range of tetracaine hydrochloride in the topical anesthetic of the present invention is about 1%.

The topical anesthetic of the present invention can advantageously be in liquid or gel form. When it is in liquid form, the carrier is preferably a water/benzyl alcohol mixture. When it is in gel form, the carrier is preferably hydroxyethyl cellulose, but could comprise other gels.

The topical anesthetic of the present invention preferably contains no cocaine. The active ingredients of the topical anesthetic of the present invention consist essentially of lidocaine, adrenaline component, and tetracaine.

The method of the present invention comprises treating a subject having a laceration, comprising applying topically to the laceration a therapeutically effective amount of a topical pharmaceutical composition (the topical anesthetic of the present invention) comprising effective, but not excessive, amounts of lidocaine hydrochloride, tetracaine hydrochloride, and an adrenaline component or other vasoconstrictor.

The Studies

Two studies were conducted to test the efficacy, side effects, and costs of the present invention (sometimes referred to as "LAT") and compare same to that of TAC. In the first study, a liquid form of the present invention was used, and in the second, a gel form of the present invention was used.

BRIEF DESCRIPTION OF FIRST STUDY (LAT LIQUID)

Study Objective: The purpose of the first study was to compare LAT (4% lidocaine hydrochloride, 1:2000 adrenaline, 1% tetracaine hydrochloride) to TAC (0.5% tetracaine hydrochloride, 1:2000 adrenaline, 11.8% cocaine) for efficacy, side effects, and costs.

Design: Randomized, prospective, double blinded clinical trial.

Setting: Inner-city Emergency Department with an EM residency program.

Types of participants: Adults with linear lacerations of the face or scalp.

Intervention: After informed consent was obtained patients had lacerations anesthetized with topical TAC or LAT according to a random numbers table.

Measurements and Main Results: A total of 95 patients were included in the study with 47 receiving TAC and 48 receiving LAT. Patients stated the number of sutures causing pain and patients and physicians rated the overall pain of suturing using a standard visual analog scale (VAS). The power of the study to determine a ranked sum difference of 15 was 0.8. Visual analog scale results and number and percentage of sutures causing pain were compared using Wilcoxon's Rank Sum Test. According to patients the percentage of sutures causing pain was significantly fewer for LAT than TAC (p=0.036). Using the visual analog scale physicians found LAT statistically more effective than TAC (p=0.093) but patients did not report a difference (p=0.266). Cost per application was $3.00 for LAT compared to $35.00 for TAC. Follow-up was accomplished in 91 of 95 patients (95%) with no reported complications for either medication.

Conclusion: LAT worked at least as well as TAC for topical anesthesia in facial and scalp lacerations. Considering the advantages of a non-controlled substance and less expense, LAT appears to be better suited than TAC for topical anesthesia in laceration repair.

DETAILED DESCRIPTION OF FIRST STUDY (LAT LIQUID)

The purpose of the first study was to compare lidocaine hydrochloride, adrenaline, tetracaine hydrochloride (LAT), in liquid form, to TAC in a prospective, randomized double blinded trial. The hypothesis was that LAT would be as effective as TAC in facial and scalp lacerations and could replace it as a safer, less costly method of painless anesthesia, while simultaneously removing the ingredient that makes it necessary to keep the solution under close scrutiny in an Emergency Department.

In the first study 4% lidocaine hydrochloride was substituted for cocaine, the recommended amount of adrenaline was retained, and the tetracaine component was increased to a 1% solution as recommended by several topical studies (11,12). The LAT was in a liquid carrier. Advantages to such a formula include all the benefits of a topical anesthetic without using a controlled substance known to produce measurable blood levels. The solution of lidocaine-adrenaline-tetracaine (LAT) could be safer and is considerably less expensive (approximately $3 for LAT, as opposed to approximately $35 for TAC).

It was found that patients had fewer percent of sutures causing pain in the LAT group than in the TAC group. On visual analog ratings physicians felt LAT less painful in suturing than TAC and patients found them about equal overall (see Tables). There was general agreement between patients and physicians in scorings. A similar number of patients in each group requested further anesthetic, necessitating injectable lidocaine. Wound complication rates were small in both the TAC and LAT groups.

Considering costs, potential for problems using controlled substances and potential for toxicity with measurable urine/blood levels with cocaine use, the formulation of the present invention appears to be a better alternative for topical anesthesia in scalp and facial lacerations.

Further study is needed in efficacy and safety including urine/serum levels with normal applications using LAT.

With avoidance of mucous membrane application and care not to exceed recommended dosages, however, there were no adverse effects in the present study with either LAT or TAC. Mixing 4% lidocaine hydrochloride with 1% tetracaine hydrochloride, (maximal effective concentrations) may theoretically increase systemic effects (37) so that use in mucous membranes with rapid absorption potential is not recommended (43,44).

Methods

The study was approved by the Louisiana State University Institutional Review Board and was performed in a county facility. The design was a prospective randomized double blinded study. One hundred patients 18 years of age and older were to be entered. Patients were included if they had lacerations located on the face or scalp, the laceration size was 7 cm or less in length, and there was no mucosal involvement.

Patients were excluded if they were felt unable to measure pain via a standard visual analog scale (22,23) secondary to alcohol intoxication, drug use, or mental illness, if they had allergies to esters or amides anesthetics, if they had contraindications to vasoconstrictor use (lacerations were more than eight hours old or grossly contaminated), or if they desired not to participate in the study.

The solutions were prepared by a pharmacist and available in sterile capped 3 cc syringes with a cotton ball for application. The TAC solution was a standard 0.5% tetracaine hydrochloride, 1:2000 epinephrine, 11.8% cocaine and the LAT solution was prepared as 4% lidocaine hydrochloride, 1:2000 epinephrine and 1% tetracaine hydrochloride.

The LAT liquid was prepared as follows:

| Component | Amount |
| --- | --- |
| 4% lidocaine HCl | 4 g |
| 1:2000 adrenaline (0.05%) | 50 cc 1:1000 |
| 1% tetracaine HCl | 1 g |
| 2% benzyl alcohol | 2 ml. |

A preserved water base to 100 cc (preserved with 0.05% methyl paraben and 0.025% propylparaben) was added in a quantity sufficient to make 100 cc of LAT solution. The benzyl alcohol is used to preserve the solution—it also has some anesthetic properties.

Solutions were randomized according to a random numbers table and patients and physicians performing suturing were blinded to which solutions were being used. Only the numbers 1–100 appeared on the capped syringes. Solutions were available in 3 cc volumes. Prior to implementing the study, physicians performing suturing were oriented to the protocols, proper solution application, and safety precautions. Only physicians directly involved in the study applied the solutions.

After proper consent was obtained, wounds were prepared based on the preference of the physician. Topical solutions were applied with small saturated pieces of cotton into and around the wound edges. Solutions remained on the wound a minimum of 10 minutes to a maximum of 30 minutes. Care was taken not to get anesthetic near mucous membranes. If the patient was still sensitive to pinprick with a 25 gauge needle at 10 minutes, more time was given. If the wound was still sensitive at 20 minutes, more of the same solution could be applied. The wound was rechecked every 10 minutes to the 30 minute time limit. If anesthesia was still not adequate, this was recorded, then 1% lidocaine was injected and the amount recorded. After the anesthesia was felt to be adequate, laceration repair was performed as deemed suitable by the physician.

Both physician and patient rated the anesthesia effectiveness during suturing utilizing a standard 10 cm linear visual analog scale (22,23). Patients also reported the number of sutures causing pain which was analyzed as percent of total sutures placed. Demographic and clinical data were collected in the Emergency Department at the time of suturing. These included age, sex, length of lacerations, location of laceration, amount of local anesthetic used, the need for additional lidocaine injectable anesthesia, the time anesthesia lasted, and any complications at the time of suturing. Patients were followed by return visits, medical records or telephone for any problems with healing of lacerations.

Statistical analysis was performed using Spearman ranked correlation coefficients to assess relationships between age, length of lacerations, amount of local anesthetic used with the responses of percent of sutures causing pain and the visual analog ratings of the patients and physicians. Wilcoxon's ranked sum test was employed in determining if continuous variables (age, length and amount) of solutions were equally distributed for each of the categorized response variables (percent causing pain and visual analog scale ratings of physicians and visual analog scale ratings of patients) (24). Fisher's Exact test was used to determine if the discrete variables (male versus female and location of laceration) were equally distributed for each categorical response variable (percent of sutures causing pain, visual analog scale ratings of physicians, and VAS ratings of patients) (25). To assess treatment effects on percent of sutures causing pain and the visual analog scales, Wilcoxon's ranked sum test was used.

To evaluate agreement between patient and physician responses in visual analog scale measurements, generalized Kappa statistics were used (26). For all analyses p<0.05 was considered statistically significant.

A power analysis was performed on the two groups to determine adequate sample size in determining a difference between the two groups, TAC versus LAT. A sample size of 95 had a power of 0.8 to tell a ranked sum difference of 15.

Results

One hundred patients were initially entered in the study. Four patients were excluded prior to analysis because they each required additional injected lidocaine. They were considered treatment failures due to inadequate anesthesia (three in the TAC group and one in the LAT group). A fifth patient was excluded due to improper data collection. Ninety-five patients were included in final statistical analysis with 48 receiving LAT and 47 receiving TAC.

Differences between the two groups could not be explained by the differences in demographic data. Males and females were equally distributed in the two groups with 40 (82%) men and 9 (18%) women receiving LAT, and thirty-six (72%) men and 14 (28%) women receiving TAC. Ages ranged from 17–69 in the LAT group with a median age of 31 and 18–74 in the TAC group with a median of 34. The mean age was 33 in the LAT group with a standard deviation of 11 and 34 in the TAC group with a standard deviation of 13. Distribution of ages, amount of solution used, length of lacerations, sex of patients, and location of lacerations were similar for the two groups (Table 1) (27,28).

TABLE 1

| | Demographics (liquid) | |
| --- | --- | --- |
| | LAT (n = 48) | TAC (n = 47) |
| ED/Treatment Failures | 2 | 3 |
| Sex | | |
| Males | 40 | 36 |
| Females | 9 | 14 |
| Ages | | |
| median | 31 | 34 |
| mean +/− STD | 33 +/− 11 | 34 +/− 13 |
| range | 17–69 | 18–74 |
| Length of Laceration | | |
| median | 2.5 cm | 2.0 cm |
| mean +/− STD | 2.6 +/− 1.2 | 2.3 +/− 0.8 |
| range | 0.5–6 cm | 1–5 cm |
| Amount of local anesthetic used | | |
| median | 1.5 cc | 1.5 cc |
| mean +/− STD | 1.6 +/− 0.9 | 1.6 +/− 0.8 |
| range | 0.2–3.0 cc | 0.3–3.0 cc |
| Location of laceration | | |
| face | 41 | 40 |
| scalp | 7 | 6 |
| Number of sutures placed | | |
| median | 6 | 6 |
| range | 1–22 | 2–18 |

Wound size, location, amount of anesthetic used, and number of sutures placed were also comparable. Length of lacerations ranged from 0.5 to 6 cm with a median of 2.5 cm, mean of 2.6±1.2 in the LAT group and a range of 1 cm to 5 cm with a median of 2.0 cm, mean of 2.3±0.8 in the TAC group. Location of the lacerations was also equally distributed with 41 (85%) involving the face and 7(15%) involving the scalp in the LAT group and 42 (88%) involving face and 6 (12%) involving scalp in the TAC group. The median number of sutures in the two groups was the same (6 in both the LAT and TAC groups, mean of 7.4±4.2, range of 1–22 in the LAT group and mean of 6.5±3.5, range of 2–18 in the TAC group). These results are summarized in Table 1.

The number of sutures causing pain was assessed statistically as a percentage. LAT was found to have fewer painful sutures than TAC (p=0.0361). The range of percent causing pain was 0–33 for LAT whereas the TAC groups had a larger range of 0–80. The median number of sutures causing pain in both groups was 0 with a range of 0–3 in the LAT group and 0–4 in the TAC group. The mean percent of sutures causing pain was 4±9 in the LAT group with a mean of 10±22 in the TAC group. Results are summarized in Table 2.

TABLE 2

Percent of sutures causing pain (liquid)

| | LAT | TAC |
| --- | --- | --- |
| Median % of sutures causing pain | 0 | 0 |
| Standard deviation of % causing pain | 4 +/− 9 | 10 +/− 22 |
| Range of # of sutures causing pain | 0–3 | 0–4 |
| Range of % of sutures causing pain | 0–33 | 0–80 |
| Mean Ranked Sum | 42.8 | 53.3 | p = 0.036 for differences between LAT versus TAC percent causing pain

Visual analog pain ratings for physicians and patients are summarized in Table 3. For physicians, the median ratings in the LAT group was 0 with a range of 0–5 cm on the visual analog scale, whereas the median of the TAC group was 0 with a range from 0–6 cm. The median for patients of the LAT group was 0 with a range of 0–4 cm on the visual analog scale, and the median of the TAC group was 0 with a range from 0–6 cm.

Comparisons of the physician scores and patient scores in the LAT versus TAC groups are shown in Table 3. For physician ranked sum ratings there was a difference between the LAT versus TAC groups showing that LAT was more effective than TAC during suturing (p=0.0093) (Table 3). For patient ranked sum ratings of TAC and LAT no statistically significant differences were detected in pain scores with p=0.266 (Table 3).

TABLE 3

Pain scores in the LAT versus TAC groups (liquid)

| | LAT | TAC |
| --- | --- | --- |
| Physician ratings | | |
| median | 0 cm | 1 cm |
| range | 0–5 cm | 0–6 cm |
| Mean ranked sum* | | |
| Patient ratings | | |
| median | 0 cm | 0 cm |
| range | 0–4 cm | 0–6 cm |
| Mean ranked sum** | 45.3 | 50.8 |

*p = 0.0093 for difference between LAT and TAC according to physicians
**p = 0.266 for difference between LAT and TAC according to patients Using weighted Kappa statistics in analysis, general agreement was found between physician and patient ratings for the LAT versus TAC groups. For overall agreement in the 2 groups 73% matched exactly. Subdividing into LAT and TAC groups 79% of LAT physician and patient scores matched exactly with a weighted kappa score of 64%. For the TAC group 66% exactly matched with a weighted kappa of 64%. These were equivalent on analysis. (26).

Follow-up was available in 91 of 95 patients entered in the study. There was one wound infection in the TAC group and one report of a hematoma in the TAC group without infection. Otherwise no problems or complications were reported in either TAC or LAT groups.

BRIEF DESCRIPTION OF SECOND STUDY
(LAT GEL)

Study Objective: The purpose of the second study was to compare LAT gel (4% lidocaine hydrochloride, 1:2000 adrenaline, 0.5% tetracaine hydrochloride) to TAC gel (0.5% tetracaine, 1:2000 adrenaline, 11.8% cocaine) for efficacy, side effects, and costs in children ages 5–17 with facial or scalp lacerations.

Design: Randomized, prospective, double blinded clinical trial.

Setting: Inner-city Emergency Department with an Emergency Medicine residency program.

Patients or other participants: Children ages 5–17 with linear lacerations of the face or scalp.

Intervention: After informed consent was obtained patients had lacerations anesthetized with topical TAC or LAT gel according to a random numbers table.

Measurements and Main Results: A total of 95 patients were included in the statistical analysis with 47 receiving TAC and 48 receiving LAT. Physicians and patients/parents separately rated the overall pain of suturing using a modified multidimensional scale for pain assessment specifically for children. Patients/parents also stated the number of sutures causing pain. The power of the study to determine a ranked sum difference of 15 was 0.8. Multidimensional rating scale results and number and percentage of sutures causing pain were compared using Wilcoxon's Rank Sum Test. According to patients no difference could be detected in percent of sutures causing pain in the LAT versus TAC group (p=0.51). Using the multidimensional scale, physicians and patients/parents found LAT statistically the same as TAC in effectiveness (p=0.80 for physicians and p=0.71 for patients). Cost per application was $3.00 for LAT compared to $35.00 for TAC. Follow-up was accomplished in 85 of 95 participants in the study with no reported complications for either medication.

Conclusion: LAT gel worked as well as TAC gel for topical anesthesia in facial and scalp lacerations. Considering the advantages of a non-controlled substance and less expense, LAT gel appears to be better suited than TAC gel for topical anesthesia in laceration repair in children.

DETAILED DESCRIPTION OF SECOND STUDY
(LAT GEL)

The purpose of the second study was to compare Lidocaine hydrochloride 4%, adrenaline 1:2000, tetracaine hydrochloride 0.5% (LAT) in a gel form to standard TAC in a gel form in a prospective, randomized double blinded trial in children ages 5–17. The hypothesis was that LAT would be as effective as TAC in facial and scalp lacerations and could replace it as a safer, less costly method of painless anesthesia, while simultaneously removing the ingredient that makes it necessary to keep the mixture under close scrutiny in an Emergency Department.

The previous study in adult patients of LAT using 1% tetracaine hydrochloride in a solution formula showed LAT to be statistically better than TAC according to physicians and by patient ratings of number of sutures causing pain. The present study was performed to see its effectiveness in children, in gel form, and with 0.5% tetracaine hydrochloride instead of 1%.

The solutions were prepared by a pharmacist and available in sterile capped 3cc syringes with a Q-tip brand applicator for application. The TAC solution was a standard 0.5% tetracaine hydrochloride, 1:2000 epinephrine, 11.8% cocaine and the LAT solution was prepared as 4% lidocaine hydrochloride, 1:2000 epinephrine and 0.5% tetracaine HCl.

The LAT gel was prepared as follows:

| Component | Amount |
| --- | --- |
| 4% lidocaine HCl | 4 g lidocaine HCl |
| 1:2000 adrenaline (0.05%) | 50 cc 1:1000 |
| 0.5% tetracaine HCl | 0.5 g tetracaine HCl |
| gel | 3 g hydroxyethyl cellulose. |

Water preserved with 0.05% methyl paraben and 0.025% propylparaben was added in a quantity sufficient to make 100 cc of LAT solution. The hydroxyethyl cellulose, when mixed with water, forms a gel. The gel form is preferable to the liquid form because the gel form stays on the laceration better, so less anesthetic needs to be used to achieve the same results.

Methods

The study was approved by the Louisiana State University Institutional Review Board and was performed in a county facility. The design was a prospective randomized double blinded clinical trial. One hundred patients 5–17 years of age were to be entered, 50 to receive TAC and 50 to receive LAT. Patients were included if they had lacerations located on the face or scalp, the laceration size was 7 cm or less in length, and there was no mucosal involvement.

Patients were excluded if they were felt unable to measure pain via a modified multidemsional pain rating scale (rated from 0 corresponding to no pain to 10 corresponding to worst pain ever), (15,46) secondary to alcohol or drug use, or mental illness, if they had allergies to ester or amide anesthetics, if they had contraindications to vasoconstrictor use (lacerations were more than eight hours old or grossly contaminated), or if they or their parents desired not to participate in the study.

A power analysis was performed on the two groups to determine adequate sample size in determining a difference between the two groups, TAC versus LAT. A sample size of 95 had a power of 0.8 to tell a ranked sum difference of 15.

The gels were prepared by a pharmacist and available in sterile capped 3 cc syringes with a cotton tipped applicator for usage. The TAC gel was a standard 0.5% tetracaine hydrochloride, 1:2000 epinephrine, 11.8% cocaine in a gel form and the LAT gel was prepared as 4% lidocaine hydrochloride, 1:2000 epinephrine and 0.5% tetracaine hydrochloride in a gel form (hydroxyethyl cellulose in both gels) with preservatives.

Gels were randomized according to a random numbers table and patients and physicians performing suturing were blinded to which gel was being used. Only the numbers 1–100 appeared on the capped syringes. Gels were available in 3 cc volumes. Prior to implementing the study, physicians performing suturing were oriented to the protocols, proper solution application, and safety precautions. Only physicians directly involved in the study monitored the application of the gels.

After proper consent was obtained, wounds were prepared based on the preference of the physician. Topical gels were applied by cotton-tipped applicators into and around the wound edges. Gels remained on the wound a minimum of 10 minutes to a maximum of 30 minutes. Care was taken not to get anesthetic near mucous membranes. If the patient was still sensitive to pinprick with a 25 gauge needle at 10 minutes, more time was given. If the wound was still sensitive at 20 minutes, more of the same gel could be applied. The wound was rechecked every 10 minutes to the 30 minute time limit. If anesthesia was still not adequate, this was recorded, then 1% lidocaine was injected and the amount recorded. After the anesthesia was felt to be adequate, laceration repair was performed as deemed suitable by the physician.

Both physician and patient or parent rated the anesthesia effectiveness during suturing utilizing a modified multidemsional pain scale (starting with 0 for no pain and ending with 10 for worst pain) (46). Patients or parents reported the number of sutures causing pain which was analyzed as percent of total sutures placed. Demographic and clinical data were collected in the Emergency Department at the time of suturing. These included age, sex, length of lacerations, location of laceration, amount of local anesthetic used, the need for additional lidocaine injectable anesthesia, the time anesthesia lasted, and any complications at the time of suturing. Patients were followed up by return visits, medical records or telephone for any problems with healing of lacerations.

Wilcoxon's ranked sum test was employed in determining if continuous variables (age, length and amount) of solutions were equally distributed for each of the categorized response variables (percent causing pain and multidimensional scale ratings of physicians and of patients) (24). Fisher's Exact test was used to determine if the discrete variables (male versus female and location of laceration) were equally distributed for each categorical response variable (percent of sutures causing pain, interval scale ratings of physicians, and pain ratings of patients) (25). To assess treatment effects on percent of sutures causing pain and the pain scale ratings, Wilcoxon's ranked sum test was used. For all analyses $p<0.05$ was considered statistically significant.

Results

One hundred patients were initially entered in the study. Five patients were excluded prior to statistical analysis because each required additional lidocaine injected and pain scales were not considered useful in judging pain. They were considered treatment failures due to inadequate anesthesia (three in the TAC group and two in the LAT group). Ninety-five patients were included in the final statistical analysis with 48 receiving LAT and 47 receiving TAC.

Differences between the two groups could not be explained by the differences in demographic data. Males and females were equally distributed in the two groups with 38 (79%) males and 10 (21%) females receiving LAT and 34 (72%) males and 13 (28%) females receiving TAC. Ages ranged from 5–16 in the LAT group with a median of 7 (interquartile range 10–5.5) and 5–17 in the TAC group with a median of 8 (interquartile range 12–6). Distribution of ages, amount of gel used, length of lacerations, sex of patients, and locations of lacerations was similar for the two groups (Table 4).

Wound size, location, amount of anesthetic used, and number of sutures placed were also comparable. Length of lacerations ranged from 0.5–4 cm with a median of 2 cm (interquartile range 2.5–1 cm in the TAC group, and a range of 0.5–5 cm with a median of 2cm (interquartile range 2.5–1.25) in the LAT group. Location of lacerations were equally distributed with 34 involving the face and 14 involving the scalp in the LAT group with 30 involving the face and 17 involving the scalp in the TAC group. The median number of sutures was 5 in the LAT group and 4 in the TAC group. These results are summarized in Table 4.

TABLE 4

Demographics (gel)

|  | LAT (n = 48) | TAC (n = 47) | p-value |
|---|---|---|---|
| ED/Treatment Failures | 2 | 3 | |
| Sex | | | |
| Males | 38 | 34 | |
| Females | 10 | 13 | 0.48* |
| Ages | | | |
| median | 7 | 8 | |
| range | 5–16 | 5–17 | |
| Interquartile Range | 10–5.5 | 12–6 | 0.18** |
| Length of Laceration | | | |
| median | 2.0 cm | 2.0 cm | |
| range | 0.5–5 cm | 0.5–4 cm | |
| Interquartile Range | 2.5–1.25 cm | 2.5–1.0 cm | 0.95** |
| Amount of local anesthetic used | | | |
| median | 1.40 cc | 1.25 cc | |
| range | 0.25–3 cc | 0.25–3.0 cc | |
| Interquartile Range | 2.0–1.0 cc | 2.0–1.0 cc | 0.89** |
| Location of laceration | | | |
| face | 34 | 30 | |
| scalp | 14 | 17 | 0.27* |
| Number of sutures placed | | | |
| median | 5 | 64 | |
| range | 1–13 | 1–15 | 0.66** |

**Using Fisher's Exact test
**Using Wilcoxon's Rank sum test

The number of sutures causing pain was assessed statistically as a percentage for each patient. No statistically significant difference was detected in the LAT versus TAC groups (p=0.51). These results are summarized in Table 5.

TABLE 5

Percent of sutures causing pain (gel)

|  | LAT | TAC |
|---|---|---|
| Median % of sutures causing pain | 0 | 0 |
| Standard deviation of % causing pain | | |
| Range of % causing pain | 1.0–0.0 | 1.0–0.0 |
| Interquartile Range of % causing pain | 0.25–0.0 | 0.20–0.0 |
| Mean Ranked Sum* | 49.57* | 46.39* |

*p = 0.51 for differences between LAT versus TAC percent causing pain (using Wilcoxon's rank sum test)

Pain scale ratings for physicians and patients are summarized in Table 6. The median rating in both the LAT and TAC groups was 2 with a range of 0–7 in both for physicians. For patients the median for the LAT and TAC groups was 2 with a range of 0–8 for LAT and 0–7 for TAC.

TABLE 6

Pain scores in the LAT versus TAC groups (gel)

|  | LAT | TAC |
|---|---|---|
| Physician ratings | | |
| median | 2 | 2 |
| range | 0–7 | 0–7 |
| Interquartile Range | 3.0–0.0 | 3.0–0.0 |
| Mean ranked sum* | 48.7* | 47.3* |
| Patient ratings | | |
| median | 2.0 | 2.0 |
| range | 0–8 | 0–7 |
| Interquartile Range | 5.0–0.0 | 3.0–0.0 |
| Mean ranked sum** | 49.0** | 46.9** |

*p = 0.80 for difference between LAT and TAC according to physicians
**p = 0.71 for difference between LAT and TAC according to patients Comparisons of the physician scores in the LAT versus TAC groups are shown in Table 6. For physician ranked sum ratings, no statistically significant difference was detected between the LAT versus TAC groups (p=0.80, interquartile range 3–0 for LAT and 3–0 for TAC). For patient ranked sum ratings of TAC and LAT no statistically significant differences were detected in pain scores (p=0.71, interquartile range 5–0 for LAT and 3–1 for TAC).

Follow-up was available in 85 of 95 patients entered in the second study. There was one wound infection in the TAC group and one in the LAT group. One patient in the TAC group reported large scar formation and requested a plastic surgical revision. No other problems or complications were reported in either the TAC or LAT groups.

When concentrations are expressed herein as percentages, they are percentages by weight unless clearly indicated otherwise.

Lidocaine hydrochloride is sometimes sold under the trademark "Xylocaine®". Tetracaine hydrochloride is sometimes sold under the trademark "Pontocaine®". The term "adrenaline component", as used herein when describing the present invention, refers to a substance consisting essentially of one or more components from the group consisting of adrenaline, epinephrine, phenylephrine, and norepinephrine. Epinephrine is the preferred adrenaline component. Vasoconstrictors other than an adrenaline component as defined herein could be used in place of the adrenaline component; in such a case, the amount of the other vasoconstrictor would be chosen to match as closely as possible the adrenaline component. Examples of other suitable vasoconstrictors include vasopressin and angiotensin. It is believed that any component which retards absorption of the lidocaine and tetracaine could be substituted for the adrenaline component; however, the inventor knows that epinephrine works and for that reason recommends it.

The adrenaline component is useful to prolong anesthetic effects.

"Lidocaine component" as used herein refers to lidocaine HCl and other forms of lidocaine which can be useful as topical anesthetics.

"Tetracaine component" as used herein refers to tetracaine HCl and other forms of tetracaine which can be useful as topical anesthetics.

The lidocaine HCl used in the experiments was purchased from Professional Compounding Center of America, Inc. in a powder form. The tetracaine HCL used in the experiments was purchased from Professional Compounding Center of America in a powder form. The adrenaline component used in the experiments was epinephrine purchased from Parke-Davis Company in a 1:2000 solution.

The 2% benzyl alcohol, the preserved water base (preserved with 0.05% methyl paraben and 0.025% propylparaben), and the hydroxyethyl cellulose (CPS 5000) were purchased from Professional Compounding Center of America.

Carboxylmethylcellulose could be used instead of hydroxyethyl cellulose to make the gel form.

Cations, such as K+, Mg++, and H+, can be added to enhance the effects of the lidocaine and tetracaine in the solutions of the present invention. For information about these cations, see the articles written by Adriani and listed in the appendix.

The route of administration of the composition of the present invention is topical. The composition of the present invention should not be injected instead of being applied topically. Injection could result in toxicity, skin sloughing from the vasoconstrictor.

The foregoing embodiments are presented by way of example only; the scope of the present invention is to be limited only by the following claims.

APPENDIX

References

1. Pryor G. J., Kilpatrick W. R., Opp DR. Local anesthesia in minor lacerations: Topical TAC vs lidocaine infiltration. Ann Emer Med 1980; 9(11): 568–571.

2. Anderson A. B., Colecchi C., Baronoski R., DeWitt T. G. Local anesthesia in pediatric patients: Topical TAC versus lidocaine. Ann Emerg Med 1990; 19(5): 519–522.

3. Hegenbarth M. A., Altieri M. F., Hawk W. H., et al. Comparison of topical tetracaine, adrenaline, and cocaine anesthesia with lidocaine infiltration for repair of lacerations in children. Ann Emerg Med 1990; 19(1): 63–67.

4. Bonadio W. A., Wagner V. Efficacy of TAC topical anesthetic for repair of pediatric lacerations. Amer J Dis Child 1933; 142: 203–205.

5. Nichols F. C., Mucha P., and Farnell M. B. TAC topical anesthetic and minor skin lacerations. Res Staff Phys 1987; 33(2): 59–66.

6. Daya M. R., Burton B. T., Schleiss M. R., DiLiberti J. H. Recurrent seizures following mucosal application of TAC. Ann Emerg Med 1988; 17(6): 646–648.

7. Tipton G. A., DeWitt G. W., Eisenstein S. J. Topical TAC solution for local anesthesia in children: prescribing inconsistency and acute toxicity. South Med J 1989; 82(11): 1344–1346.

8. Dailey R. H. Fatality secondary to misuse of TAC solution. Ann Emerg Med 1988; 17(2): 159–160.

9. Altieri M., Bogema S., Schwartz R. H. TAC topical anesthesia produces positive urine tests for cocaine. Ann Emerg Med 1990; 19(5): 577–579.

10. Fitzmaurice L. S., Wasserman G. S., Knapp J. F., et al. TAC use and absorption of cocaine in a pediatric emergency department 1990; 19(5): 515–518.

11. Terndrup T. E., Mariani P. J., Walls H. C., et al. Plasma cocaine levels following application of topical anesthesia in a swine laceration model. Amer J Emerg Med 1991; 9: 539–543.

12. Terndrup T. E., Walls H. C., Mariani P. J., et al. Plasma cocaine and tetracaine levels following application of topical anesthesia in children. Ann Emerg Med 1992; 21(2): 162–166.

13. Barker W., Rodenhearver G. T., Edgerton M. T. et al. Damage to tissue defenses by a topical anesthetic agent. Ann Emerg Med 1982; 11(6): 307–310.

14. Martin J. R., Doezema D., Tandberg D., et al. The effect of local anesthetics on bacterial proliferation: TAC versus lidocaine. Ann Emerg Med 1990; 19(9): 987–990.

15. Smith S. M., Barry R. C. A comparison of three formulations of TAC for anesthesia of minor lacerations in children. Ped Emerg Care 1990; 6(4): 266–270.

16. Bonadio W. A., Wagner V. Half-strength TAC topical anesthetic. Clin Ped 1988; 27(10): 495–498.

17. Schaffer D. J. Clinical comparison of TAC anesthetic solutions with and without cocaine. Ann Emerg Med 1985; 14(11): 1077–1080.

18. Ernst A. A., Crabbe L. H., Winsemius D. K., et al. Comparison of tetracaine, adrenaline, and cocaine with cocaine alone for topical anesthesia. Ann Emerg Med 1990; 19(1): 51–54.

19. White W. B., Iserson K. V., Criss E. Topical anesthesia for laceration repair: Tetracaine versus TAC. Am J Emerg Med 1986; 4: 319–322.

20. Bonadio W. A., Wagner V. Efficacy of tetracaine adrenaline cocaine topical anesthetic without tetracaine for facial laceration repair in children. Pediatrics 1990; 86(6): 856–857.

21. Bonadio W. A., Wagner V. R. Adrenaline-cocaine gel topical anesthetic for dermal laceration repair in children. Ann Emerg Med 1992; 21(12): 1435–1438.

22. Scott J., Huskisson E. C. Graphic representation of pain. Pain 1976; 2: 175–184.

23. Revill S. I., Robinson J. O., Rosen M., et al. The reliability of a linear analogue for evaluating pain. Anesthesia 1976; 31: 1191–1198.

24. Agresti A., Mehta C. R., Patel Nr. Exact inference for contingency tables with ordered categories. J Amer Statis Assoc 1990; 85(410): 453–458.

25. Mehta C. R., Patel N. A network algorithm for performing Fisher's exact test in r x c contingency tables. J Amer Statis Assoc 1984; 78 (382): 427–434.

26. Cohen J. Weighted kappa: Nominal scale agreement with provision for scaled disagreement or partial credit. Psychol Bull 1968; 70: 213.

27. Koch G. G., Carr G. J., Amara I. A., et al. Categorical Data Analysis. In chapter 18, page 394 Statistical Methodology in the Pharmaceutical Sciences, ed D. Berry, Marchell Dekker Inc, New York.

28. Cox D. R., McCullough P. Some aspects of covariance. Biometrics 1982; 38: 541–561.

29. Wehner D., Hamilton G. C. Seizures following topical application of local anesthetics to burn patients. Ann Emerg Med 1984; 13(6): 456–458.

30. Dronen S. C. Complications of TAC (letter). Ann Emerg med 1983; 12: 333.

31. Bonadio W. A., Wagner V. When TAC drips into the eye. Amer J Emerg Med 1990; 8:371.

32. Jacobsen S. Errors in emergency practice. Emerg Med 1987; 19: 109.

33. Thrasher J. B., Peterson M. E. Donatucci C. F. Lidocaine as a topical anesthetic for bladder biopsies. J Urol 1991; 145: 1209–1210.

34. Rowbotham M. D., Fields H. L. Topical lidocaine reduces pain in post-herpetic neuralgia. Pain 1989; 38: 297–301.

35. Brofeldt B. T., Cornwell P., Boherty D., et al. Topical lidocaine in the treatment of partial-thickness burns. J Burn Care Rehabil 1989; 10: 63–8.

36. Prefontaine M., Fung-Kee-Fung M., Moher D. Comparison of topical xylocaine with placebo as a local anesthetic in colposcopic biopsies. CJS 1991; 34 (2): 163–5.

37. Adriani J., Zepernick R. Clinical effectiveness of drugs used for topical anesthesia. JAMA 1964; 188(8): 711–716.

38. Carabelli A. A. The use of pontocaine in subposologic quantities for bronchoscopy and bronchography. Anesthesiology 1952; 13: 169–183.

39. Hansen L. M., Reynolds F. B., Foldvari M. Topical liposomal tetracaine for IV cannulation. Can J Anes 19; (abstract): S64.

40. Smith M., Wolfram W., Rose R. Toxicity-Seizures in an infant caused by (or related to) oral viscous lidocaine use. J Emerg Med 1992; 10: 587–590.

41. Mofenson H. C., Caraccio T. R., Miller H., Greensher J. Lidocaine toxicity from topical mucosal application. Clin Pediatr 1983; 22(3): 190–192.

42. Garrettson L. K., McGee E. B. Rapid onset of seizures following aspiration of viscous lidocaine. Clin Toxicol 1992; 30(3): 413–422.

43. Adriani J., Campbell D. Fatalities following topical application of local anesthetics to mucous membranes. JAMA 1956; 162 (17): 1527–1530.

44. Campbell D., Adriani J. Absorption of local anesthetics. JAMA 1958; 168(7): 873–877.

45. DiFazio C. A. Local anesthetics: Action, metabolism and toxicity. Otolarynogol Clin N Amer 1981; 14(3): 515–519.

46. McGrath P. A., deVeber L. L., Hearn M. Multidimensional pain assessment in children. Adv Pain Res Ther 1985; 9: 387–393.

I claim:

1. A pharmaceutical composition for use as a topical anesthetic, the composition comprising an effective therapeutic combination of:
   (a) a lidocaine component;
   (b) a vasoconstrictor; and
   (c) a tetracaine component,
   wherein the lidocaine component, vasoconstrictor, and tetracaine component are in a gel base.

2. The pharmaceutical composition of claim 1, wherein: the lidocaine component is lidocaine hydrochloride and is present in an amount of at least 1% by weight of the composition.

3. The pharmaceutical composition of claim 1, wherein: the vasoconstrictor is an adrenaline component and is present in an amount of at least 0.01% by weight of the composition.

4. The pharmaceutical composition of claim 1, wherein: the tetracaine component is tetracaine hydrochloride and is present in an amount of at least 0.25% by weight of the composition.

5. The pharmaceutical composition of claim 1, wherein: the lidocaine component is lidocaine hydrochloride and is present in an amount of about 1–10% by weight of the composition.

6. The pharmaceutical composition of claim 1, wherein: the vasoconstrictor is an adrenaline component and is present in an amount of about 0.01–0.1% by weight.

7. The pharmaceutical composition of claim 1, wherein: the tetracaine component is tetracaine hydrochloride and is present in an amount of about 0.25–4% by weight.

8. The pharmaceutical composition of claim 1, comprising:
   about 4% by weight lidocaine hydrochloride,
   about 0.05% by weight adrenaline component, and
   about 1% by weight tetracaine hydrochloride.

9. The pharmaceutical composition of claim 1, further comprising:
   preservative means for preserving the composition.

10. A pharmaceutical gel composition comprising:
    (a) 1% to 10% by weight lidocaine hydrochloride;
    (b) a vasoconstrictor; and
    (c) 0.25% to 4% by weight tetracaine hydrochloride; and
    (d) a suitable, inert, pharmaceutically acceptable gel carrier for the lidocaine hydrochloride, vasoconstrictor, and tetracaine hydrochloride.

11. A pharmaceutical composition for use as a topical anesthetic, the composition comprising as active ingredients:
    (a) an effective amount of lidocaine hydrochloride;
    (b) an effective amount of a vasoconstrictor; and
    (c) an effective amount of tetracaine hydrochloride,
    wherein the lidocaine hydrochloride, vasoconstrictor, and tetracaine hydrochloride are in a gel base.

12. A method of inducing local anesthesia in a subject, comprising applying topically to the subject a therapeutically effective amount of a topical anesthetic pharmaceutical gel composition comprising lidocaine hydrochloride, tetracaine hydrochloride, and a vasoconstrictor.

13. A method of inducing local anesthesia in a subject, comprising applying topically to the subject a therapeutically effective amount of a topical anesthetic pharmaceutical gel composition comprising lidocaine hydrochloride, tetracaine hydrochloride, and a vasoconstrictor, wherein the pharmaceutical composition comprises:
    (a) 1% to 10% by weight lidocaine hydrochloride; and
    (b) 0.25% to 4% by weight tetracaine hydrochloride.

14. The method of claim 12, wherein the topical anesthetic comprises:
    about 4% by weight lidocaine hydrochloride, and
    about 1% by weight tetracaine hydrochloride.

15. The method of claim 12, wherein the topical anesthetic is not applied to mucous membranes.

16. A pharmaceutical gel composition for use us a topical anesthetic, the composition comprising as active ingredients:
    (a) 1% to 10% by weight of a lidocaine component;
    (b) 0.25% to 4% by weight of a tetracaine component;
    (c) an effective amount of a component for retarding absorption of the lidocaine component and the tetracaine component.

17. The composition of claim 16, comprising:
    about 4% by weight lidocaine hydrochloride, and
    about 1% by weight tetracaine hydrochloride.

18. The method of claim 12, wherein:
    the lidocaine hydrochloride is present in an amount of about 2–6% by weight of the composition;
    the vasoconstrictor is an adrenaline component and is present in an amount of about 0.01–0.1% by weight of the composition;

the tetracaine hydrochloride is present in an amount of about 0.5–2% by weight of the composition.

19. The method of claim 13, wherein:

the lidocaine hydrochloride is present in an amount of about 2–6% by weight of the composition;

the vasoconstrictor is an adrenaline component and is present in an amount of about 0.01–0.1% by weight of the composition;

the tetracaine hydrochloride is present in an amount of about 0.5–2% by weight of the composition.

20. The pharmaceutical composition of claim 16, wherein:

the lidocaine component is lidocaine hydrochloride and is present in an amount of about 2–6% by weight of the composition;

the component for retarding absorption of the lidocaine component and the tetracaine component is an adrenaline component and is present in an amount of about 0.01–0.1% by weight of the composition;

the tetracaine component is tetracaine hydrochloride and is present in an amount of about 0.5–2% by weight of the composition.

21. The pharmaceutical composition of claim 1, wherein;

the lidocaine component is lidocaine hydrochloride and is present in an amount of about 2–6% by weight of the composition;

the vasoconstrictor is an adrenaline component and is present in an amount of about 0.01–0.1% by weight of the composition;

the tetracaine component is tetracaine hydrochloride and is present in an amount of about 0.5–2% by weight of the composition.

22. The pharmaceutical composition of claim 10, wherein:

the lidocaine hydrochloride is present in an amount of about 2–6% by weight of the composition;

the vasoconstrictor is an adrenaline component and is present in an amount of about 0.01–0.1% by weight of the composition;

the tetracaine hydrochloride is present in an amount of about 0.5–2% by weight of the composition.

23. The pharmaceutical composition of claim 11, wherein:

the lidocaine hydrochloride is present in an amount of about 2–6% by weight of the composition;

the vasoconstrictor is an adrenaline component and is present in an amount of about 0.01–0.1% by weight of the composition;

the tetracaine hydrochloride is present in an amount of about 0.5–2% by weight of the composition.

24. The method of claim 12, wherein:

the lidocaine hydrochloride is present in an amount of about 2–6% by weight of the composition;

the vasoconstrictor is an adrenaline component and is present in an amount of about 0.01–0.1% by weight of the composition;

the tetracaine hydrochloride is present in an amount of about 0.5–2% by weight of the composition.

25. The method of claim 13, wherein:

the lidocaine hydrochloride is present in an amount of about 2–6% by weight of the composition;

the vasoconstrictor is an adrenaline component and is present in an amount of about 0.01–0.1% by weight of the composition;

the tetracaine hydrochloride is present in an amount of about 0.5–2% by weight of the composition.

26. The pharmaceutical composition of claim 16, wherein:

the lidocaine component is lidocaine hydrochloride and is present in an amount of about 2–6% by weight of the composition;

the component for retarding absorption of the lidocaine component and the tetracaine component is an adrenaline component and is present in an amount of about 0.01–0.1% by weight of the composition;

the tetracaine component is tetracaine hydrochloride and is present in an amount of about 0.5–2% by weight of the composition.

* * * * *